United States Patent
Meredith et al.

(10) Patent No.: US 9,668,472 B2
(45) Date of Patent: Jun. 6, 2017

(54) POLYAMIDE AND POLYIMIDE STICKER ADJUVANTS

(71) Applicant: Huntsman Petrochemical LLC, The Woodlands, TX (US)

(72) Inventors: Matthew T. Meredith, Spring, TX (US); Alan J Stern, Magnolia, TX (US); Dilek Saylik, Meadow Heights (AU)

(73) Assignee: Huntsman Petrochemical LLC, The Woodlands, TX (US)

( * ) Notice: Subject to any disclaimer, the term of this patent is extended or adjusted under 35 U.S.C. 154(b) by 11 days.

(21) Appl. No.: 14/420,916

(22) PCT Filed: Nov. 6, 2013

(86) PCT No.: PCT/US2013/065175
§ 371 (c)(1),
(2) Date: Feb. 11, 2015

(87) PCT Pub. No.: WO2014/070451
PCT Pub. Date: May 8, 2014

(65) Prior Publication Data
US 2015/0230456 A1    Aug. 20, 2015

Related U.S. Application Data

(60) Provisional application No. 61/721,152, filed on Nov. 1, 2012, provisional application No. 61/826,711, filed on May 23, 2013.

(51) Int. Cl.
C08G 69/40 (2006.01)
C08G 73/10 (2006.01)
A01N 43/54 (2006.01)
A01N 43/653 (2006.01)
A01N 25/24 (2006.01)

(52) U.S. Cl.
CPC ............ *A01N 25/24* (2013.01); *A01N 43/54* (2013.01); *A01N 43/653* (2013.01); *C08G 69/40* (2013.01); *C08G 73/10* (2013.01); *C08G 2310/00* (2013.01)

(58) Field of Classification Search
CPC ...... A01N 25/24; A01N 43/54; A01N 43/653; C08G 69/40; C08G 73/10; C08G 2310/00
See application file for complete search history.

(56) References Cited

U.S. PATENT DOCUMENTS

| | | | |
|---|---|---|---|
| 3,806,456 A * | 4/1974 | Vogel | B01D 17/047 252/77 |
| 3,812,082 A * | 5/1974 | Jones | C08G 18/346 528/125 |
| 4,151,173 A | 4/1979 | Vogel | |
| 4,374,741 A | 2/1983 | Rieder | |
| 4,789,721 A | 12/1988 | Waddill et al. | |
| 5,053,484 A * | 10/1991 | Speranza | C08G 69/40 528/335 |
| 5,093,382 A | 3/1992 | Speranza et al. | |
| 6,399,713 B1 | 6/2002 | MacQueen et al. | |
| 6,423,304 B1 * | 7/2002 | Shah | A61K 8/042 424/400 |
| 8,247,459 B2 | 8/2012 | Kostansek | |
| 2004/0186263 A1 | 9/2004 | Pavlin | |
| 2007/0244216 A1 | 10/2007 | Stern | |
| 2009/0035380 A1 | 2/2009 | Kostansek | |
| 2011/0105333 A1 | 5/2011 | Israels et al. | |
| 2012/0108431 A1 | 5/2012 | Williams et al. | |

FOREIGN PATENT DOCUMENTS

| | | |
|---|---|---|
| EP | 2020177 A | 2/2009 |
| JP | 2001-172104 A | 6/2001 |
| WO | 02/059181 A | 8/2002 |
| WO | 2006/080917 A | 8/2006 |
| WO | 2007/109051 A | 9/2007 |

* cited by examiner

*Primary Examiner* — Paul A Zucker
*Assistant Examiner* — Mark Luderer
(74) *Attorney, Agent, or Firm* — Huntsman International LLC (57) ABSTRACT

A sticker adjuvant that may be used in agrochemical compositions is disclosed. The sticker adjuvant is a polyether amide or a polyether imide formed by the reaction of a polyether polyamine with a polyfunctional monomer. The polyfunctional monomer may be a polyacid, a di-functional acyl halide, an acid anhydride, a poly(acid anhydride) and a mixture thereof.

22 Claims, 2 Drawing Sheets

POLYAMIDE AND POLYIMIDE STICKER ADJUVANTS

CROSS-REFERENCE TO RELATED APPLICATIONS

This application is the National Phase of International Application PCT/US2013/065175 filed Nov. 6, 2013 which designated the U.S. and which claims priority to U.S. App. Ser. No. 61/826,711 filed May 23, 2013 and U.S. App. Ser. No. 61/721,152 filed Nov. 1, 2012. The noted applications are incorporated herein by reference.

FIELD

Embodiments described herein are generally related to agricultural adjuvants. More specifically, a novel type of sticker adjuvant is described.

BACKGROUND

A wide range of chemicals are applied to plants to encourage growth, discourage growth, and/or discourage pests. Many of these chemicals are active by contact with plant leaves. Usually, contact for some minimum amount of time is necessary for full activity. Sticker adjuvants are widely used to slow or prevent the active ingredient from washing off the plant surface during rain or irrigation.

Older, simpler sticker adjuvants used included fatty acids and their salts, mineral oils and drying oils (such as tung oil and linseed oil). More recent sticker adjuvants include latex polymers, polymeric terpenes, alkylphenol alkoxylates (such as nonylphenol ethoxylate condensate polymers), fatty acid derivatives, gums and polysaccharides.

However, these currently used sticker adjuvants have limited formulation abilities and the alkylphenol alkoxylates, such as the popular sticker adjuvant is based on nonylphenol ethoxylate condensate polymers, have been restricted in the various regions.

SUMMARY

Embodiments of the present invention disclose a sticker adjuvant that is a polyether amide or a polyether imide formed by the reaction of a polyether polyamine with a polyfunctional monomer. The polyfunctional monomer may be a polyacid, a di-functional acyl halide, an acid anhydride, a poly(acid anhydride) and a mixture thereof.

Embodiments of the present invention further disclose a spreader-sticker adjuvant that includes a sticker adjuvant and a spreader adjuvant. The sticker adjuvant is a polyether amide or a polyether imide formed by the reaction of a polyether polyamine with a polyfunctional monomer such as a polyacid, a di-functional acyl halide, an acid anhydride, a poly(acid anhydride) and a mixture thereof. The spreader adjuvant may be a nonionic or anionic surfactant. The spreader-sticker adjuvant may further include a solvent.

Embodiments of the present invention further disclose an agrochemical composition that includes a sticker adjuvant, an active ingredient, a spreader adjuvant and a solvent. The sticker adjuvant is a polyether amide or a polyether imide formed by the reaction of a polyether polyamine with a polyfunctional monomer such as a polyacid, a di-functional acyl halide, an acid anhydride, a poly(acid anhydride) and a mixture thereof. The agrochemical composition may be an emulsifiable concentrate or a suspension concentrate.

DETAILED DESCRIPTION

The articles "a" and "an" are used herein to refer to one or to more than one (i.e. to at least one) of the grammatical object of the article. By way of example, "a polyether polyamine" means polyether polyamine or more than one polyether polyamine.

Sticker adjuvants are agricultural adjuvants that promote adhesion of active ingredients to plant surfaces. Embodiments of the present invention disclose a sticker adjuvant that is a polyether amide or a polyether imide formed from reacting a polyether polyamine with a polyfunctional monomer selected from the group consisting of a polyacid, a di-functional acyl halide, an acid anhydride, a poly(acid anhydride) and a mixture thereof. Such sticker adjuvants, when applied to test materials that mimic surfaces of leaves and fruits, show favorable resistance to water wash-off and are expected to provide favorable sticking for active ingredients.

Embodiments of the present invention include a sticker adjuvant formed by the reaction of a polyether polyamine with a polyfunctional monomer. The polyether polyamine may be polyether diamine. Useful polyether diamines include polyoxyalkylene diamines such as polyethylene oxide-polypropylene oxide copolymers that are co-terminated by amine groups. Such polyether diamines may have the formula: $H_2N(PO)_x(EO)_y(PO)_zNH_2$, wherein x=0 to 10, y=0 to 40 and z=0 to 10, EO=ethylene oxide and PO=propylene oxide. The polyether polyamines may also be other polyethylene oxide or polypropylene oxide polymers co-terminated by amine groups. Representative polyether diamines use ethylene oxide (EO) and propylene oxide (PO) include:

Other types of polyether polyamines or ether oligomers may be used. A diamine of polytetrahydrofuran, alone or copolymerized with other alkylene oxide or olefinic monomers, may be used. Any primary polyamine having a hydrocarbon chain with some ether oxygen atoms included may be used. The oxygen atoms may be spaced at regular intervals, so that the polyether polyamine has a single repeating monomer unit, or the oxygen atoms may be spaced at differing intervals, which may be random or distributed according to a repeating pattern. Thus, the polyether polyamine may be a diamine of an ether copolymer, which may be random, block, repeating, or alternating, or of an ether multipolymer having three or more different ether monomer units.

The oxygen atoms of the polyether component of the polyether polyamine may be replaced, altogether or in part, with other electronegative species such as sulfur. Thus, a polythioether polyamine may be used as a reactant for making a useful embodiment.

Commercial examples of such polyether polyamines may include JEFFAMINE® polyetheramines and ELASTA-MINE® amines that are commercially available from Huntsman Corporation of The Woodlands, Tex. The ether units of these amines are ethylene oxide units, propylene oxide units or mixtures thereof. JEFFAMINE® polyetheramines are typically have oxypropylene units or mixtures of oxyethylene and oxypropylene units. ELASTAMINE® amines typically have oxyethylene units. Particular JEFFAMINE® polyetheramines that may be used include D-230, D-400, ED-600, ED-900, and ED-2003. The JEFFAMINE® D-series polyetheramines have the general formula:

wherein x=2 to 8, in particular, x=~2.5 for D-230 and x=~6.1 for D-400.

The JEFFAMINE® ED-series polyetheramines have the general formula:

wherein y=5 to 40 and x+z=3 to 8. In particular, ED-600 has y=~9.0 and x+z=~3.6; ED-900 has y=~12.5 and x+z=~6.0; and ED-2003 has y=~39 and x+z=~6.0.

Particular ELASTAMINE® amines that may be used include HE-1000 and HE-1700. ELASTAMINE® amines are mixtures of diamines and triamines. The diamine portion has the general formula:

wherein n=15 to 50. ELASTAMINE® HE-1000 amine has n=~21.4 and ELASTAMINE® HE-1700 amine has n=~37.3. ELASTAMINE® HE-1000 is an amine of approximately 1000 average molecular weight, based on a PEG poly(ethylene glycol). It is a mixture of diamine and triamine, and it contains a significant amount of secondary amine as well as primary amine. ELASTAMINE® HE-1700 is an amine of approximately 1700 average molecular weight, based on a PEG poly(ethylene glycol). It is a mixture of diamine and triamine, and it contains a significant amount of secondary amine as well as primary amine.

The polyether polyamines may have primary or secondary amines, and mixtures of polyether polyamines may be used.

The polyether polyamines are reacted with a polyfunctional monomer to form an amide or an imide. Such polyfunctional monomers may include polyacids, di-functional acyl halides, acid anhydrides, poly(acid anhydrides) and mixtures thereof to form the sticker adjuvants.

In embodiments of the present invention, the polyacid or acid anhydride may be a $C_4$-$C_{54}$ polycarboxylic acid or acid anhydride, such as a $C_6$-$C_{54}$ polycarboxylic acid or acid anhydride, or a $C_{18}$-$C_{54}$ polycarboxylic acid or acid anhydride.

In embodiments of the present invention, the polyacid may be a diacid. The diacid may be a $C_4$-$C_{54}$ dicarboxylic acid such as succinic acid, adipic acid, terphthalic acid, sebacic acid, and dodecanoic acid.

In embodiments of the present invention, the polyacid may be a dimerized fatty acid. Suitable dimerized fatty acids may include $C_{36}$ dicarboxylic fatty acids produced from dimerization of unsaturated $C_{18}$ monocarboxylic fatty acids from tall oil. A representative dimerized fatty acid has this structure.

Examples of a commercially available dimerized fatty acids are UNIDYME™ 14 dimer acid and UNIDYME™ 18 dimer acid from Arizona Chemical of Jacksonville, Fla. UNIDYME™ 18 dimer acid is a dimerized fatty acid containing dimerized $C_{18}$ fatty acids from tall oil in differing contents. These dimerized fatty acids may have the following structures:

The polyfunctional monomers used herein may include di-functional acyl halides, such as acyl chlorides, may also be used in place of polyacids. Bi-functional species such as acid/acyl halides, a molecule with a carboxylic acid group and an acyl halide group, may also be used.

The polyfunctional monomers used herein may include acid anhydrides. Acid anhydrides include mono-anhydrides such as maleic anhydride, succinic anhydride, or dodecenyl succinic anhydride. Another mono-anyhydride that may be used is polyisobutenyl succinic anhydride (PIBSA), available from the Lubrizol Corporation, Wickliffe, Ohio where n=1 to 40, or n=15 to 20.

Poly(acid anhydrides) may also be used. An example of a usable poly(acid anhydride) is PA-18, a linear polyanhydride resin available from Chevron Phillips Chemical Company LP of The Woodlands, Tex. PA-18 is a solid linear polyanhydride resin derived from 1-octadecene and maleic anhydride in a 1:1 molar ratio. PA-18 has the general formula:

where n=50-150.

Embodiments of the present invention allow for the use of mixtures of such polyfunctional monomers (polyacids, di-functional acyl halides, acid anhydrides, and poly(acid anhydrides)).

The polyether polyamines are reacted with a polyfunctional monomer to form a polyether amide or a polyether imide. In general, the polyacid and di-functional acyl halides react with the polyether polyamine to form an amide linkage. The acid anhydride and/or poly(acid anhydride) react with the polyether polyamine to form an amide or an imide linkage. Whether an amide or imide linkage is formed may depend on the temperature of reaction.

The sticker adjuvant may be made by combining a polyether amine and a polyfunctional monomer in a container and heating to a temperature between about 100° C. and about 300° C. Temperatures up to 500° C. may be used, with lesser yield of the sticker adjuvant molecules due to alternate reaction pathways that become more prominent at higher temperatures. Subsequent separations, such as extractions and/or distillations, may be employed in embodiments where significant alternative reactions occur. Pressure is generally between ambient pressure and about 60 psig. If multiple polyether amines and/or multiple polyfunctional monomers are reacted, they are usually used in molar parity, which is to say about the same number of moles of each reactive ingredient, but an excess of one ingredient or another may be used, if convenient. In such embodiments, the excess ingredient will not participate in the reaction, or may react with itself. A representative reaction is as follows:

-continued

When a target property, such as viscosity or acid number, is reached, the reaction may be discontinued by cooling the reaction mixture below about 100° C.

A solvent (as described in more detail later) may be added to facilitate pouring or flowing as the reaction proceeds.

In embodiments of the present invention, the sticker adjuvants may have portions that are not polyether, amide, or imide linkages. Typically, however, amide or imide linkages provide at least about 5% of the atoms in each sticker adjuvant molecule. Said another way, at least 5% of the atoms in each sticker adjuvant molecule are part of an amide or imide linkage. The amide or imide linkage typically provides no more than about 50% of the atoms in a sticker adjuvant molecule. The ratio of carbon atoms to oxygen atoms in an ether embodiment is typically from about 10 to about 50, such as about 20. In some cases, a polyether portion and a hydrocarbon portion may be joined by an amide or imide linkage to form a repeating unit, which may be repeated any number of times to achieve a desired property.

In embodiments of the present invention, the sticker adjuvants typically have an average molecular weight of at least about 1,000. Some embodiments have an average molecular weight between about 5,000 and about 10,000. As molecular weight per amide linkage increases, water solubility increases, so the molecular weight per amide linkage is typically about 800 to about 1,200.

In embodiments of the present invention, the electronegative species may be at least about 10 mole percent of each sticker adjuvant molecule. That is, at least about one atom in ten of the sticker adjuvant molecule is an electronegative atom, such as oxygen or sulfur. It is thought that the electronegative species in the molecular backbone of the sticker adjuvant provide affinity with electropositive components of the plant cuticle, enhancing the sticking function of the adjuvant.

When polycarboxylic acids and/or amines are used, combinations of higher order components that do not result in excessive crosslinking are useful for making the adjuvants described herein. A tri-functional or polyfunctional component may be reacted with a mono-functional component to avoid excessive molecular weight build. Mono amines may be reacted with polyacids or polyanhydrides, or polyamines may be reacted with mono-acids or monoanhydrides. In one embodiment, a low molecular weight acid trimer may be reacted with a polyether monoamine, such as a JEFFAMINE® M-series polyetheramine, for example M-2070, to form a three-branched molecule having a molecular weight in the above range while having a suitable combination of water insolubility and sticker adjuvant functionality. JEFFAMINE® M-2070 polyetheramine is a monoamine that has the general formula:

wherein R is $CH_3$, x=~31 and y=~10. JEFFAMINE® M-2070 has a molecular weight of 2000 and is predominately polyethylene glycol (PEG) based.

In embodiments of the present invention, sticker adjuvants may further include a solvent. A solvent may be added to reduce the viscosity of the sticker adjuvant. Suitable solvents may include petroleum-based solvents such as Aromatic 150 Fluid (Solvesso™ 150 Fluid), available from ExxonMobil Chemical Company of Houston, Tex., or paraffinic solvents such as SUNSPRAY® 7N solvent from Sunoco, Inc. of Philadelphia, Pa. Other suitable solvents include methylated seed oils (MSO's) such as SG1000 from Ag Environmental Products L.L.C. of Omaha, Nebr. The solvent may be 20% to 80% of the final formulation and may include combinations of such petroleum-based solvents and MSO's. One skilled in the art, with the benefit of this disclosure will recognize suitable solvents for use with embodiments of the present invention.

Embodiments of the present invention further disclose spreader-sticker adjuvants. The spreader-sticker adjuvants have a sticker adjuvant and a spreader adjuvant. The spreader adjuvant may be a nonionic surfactant or an anionic surfactant. Nonionic surfactants include alcohol ethyoxylates with low hydrophilic-lipophilic balance (HLB) ratios, and anionic surfactants include calcium alkylbenzenesulfonates. One skilled in the art will recognize suitable nonionic and anionic surfactants to use as spreader adjuvants in embodiments of the present invention.

The spreader-sticker adjuvants may further include a solvent as described above.

The spreader-sticker adjuvants disclosed herein may be formulated into a spreader-sticker emulsifiable concentrate (EC) by combining the sticker adjuvant with a spreader adjuvant such as nonionic and/or anionic surfactant, and a suitable solvent.

Embodiments of the present invention further disclose an agrochemical composition including a sticker adjuvant, a solvent, a spreader adjuvant and an active ingredient.

Active ingredients that may be used with the sticker adjuvants described herein include fungicides, herbicides, insecticides, algicides, molluscicides, miticides, rodenticides, and insect repellents.

Usable fungicides include, but are not limited to, azoxystrobin, trifloxystrobin, kresoxim methyl, famoxadone, metominostrobin and picoxystrobin, carbendazim, thiabendazole, dimethomorph, vinclozolin, iprodione, dithiocarbamate, imazalil, prochloraz, fluquinconazole, epoxiconazole, flutriafol, azaconazole, bitertanol, bromuconazole, cyproconazole, difenoconazole, hexaconazole, paclobutrazole, propiconazole, tebuconazole, triadimefon, trtiticonazole, fenpropimorph, tridemorph, fenpropidin, mancozeb, metiram, chlorothalonil, thiram, ziram, captafol, captan, folpet, fluazinam, flutolanil, carboxin, metalaxyl, bupirimate, ethirimol, dimoxystrobin, fluoxastrobin, orysastrobin, metominostrobin, prothioconazole, 8-(2,6-diethyl-4-methyl-phenyl)tetrahydropyrazolo[1,2-d][1,4,5]oxadiazepi-ne-7,9-dione, 2,2,-dimethyl-propionic acid-8-(2,6-diethyl-4-methyl-phenyl)-9-oxo-1,2,4,5-tetrahydro-9H-pyrazolo-[1,2 d][1,4,5]oxadiazepine-7-yl ester and metalaxyl.

Usable herbicides include, but are not limited to, fluzifop, mesotrione, fomesafen, tralkoxydim, napropamide, amitraz, propanil, cyprodanil, pyrimethanil, dicloran, tecnazene, toclofos methyl, flamprop M, 2,4-D, MCPA, mecoprop, clodinafop-propargyl, cyhalofop-butyl, diclofop methyl, haloxyfop, quizalofop-P, indol-3-ylacetic acid, 1-naphthylacetic acid, isoxaben, tebutam, chlorthal dimethyl, benomyl, benfuresate, dicamba, dichlobenil, benazolin, triazoxide, fluazuron, teflubenzuron, phenmedipham, acetochlor, alachlor, metolachior, pretilachlor, thenylchlor, alloxydim, butroxydim, clethodim, cyclodim, sethoxydim, tepraloxydim, pendimethalin, dinoterb, bifenox, oxyfluorfen, aciflurofen, fluoroglycofen-ethyl, bromoxynil, ioxynil, imazamethabenz-methyl, imazapyr, imazaquin, imazethapyr, imazapic, imazamox, flumioxazin, flumiclorac-pentyl, picloram, amodosulfuron, chlorsulfuron, nicosulfuron, rimsulfuron, triasulfuron, triallate, pebulate, prosulfocarb, molinate, atrazine, simazine, cyanazine, ametryn, prometryn, terbuthylazine, terbutryn, sulcotrione, isoproturon, linuron, fenuron, chlorotoluron, metoxuron, N-phosphonomethylglycine and its salts (glyphosate), glufosinate, chlormequat chloride, paraquat, diquat, trifloxysulfuron, fomesafen, mesotrione and fenuron.

Usable insecticides include, but are not limited to, abamectin, acephate, acetamiprid, acrinathrin, alanycarb, aldicarb, allethrin, alpha-sypermethrin, amitraz, asulam, azadirachtin, azamethiphos, azinphos-ethyl, azinphos-methyl, bendiocarb, benfuracarb, bensultap, beta-cyfluthrin, beta-cypermethrin, bifenthrin, bioallethrin, bioresmethrin, bistrifluron, borax, buprofezin, butoxycarboxim, cadusafos, carbaryl, carbofuran, chlorpropham, clothianidin, cyfluthrin, cyhalothrin, cyprmethrin, deltamethrin, diethofencarb, diflubenzuron, dinotefuran, emamectin, endosulfan, fenoxycarb, fenthion, fenvalerate, fipronil, halfenprox, heptachlor, hydramethylnon, imidacloprid, imiprothrin, isoprocarb, lambda cyhalothrin, methamidophos, methiocarb, methomyl, nitenpyram, omethoate, permethrin, pirimicarb, pirimiphos methyl, propoxur, tebufenozide, thiamethoxam, thiodicarb, triflumoron, and xylylcarb.

Usable algicides include, but are not limited to, bethoxazin, copper dioctanoate, copper sulfate, cybutryne, dichlone, dichlorophen, endothal, fentin, hydrated lime, nabam, quinoclamine, quinonamid, simazine, triphenyltin acetate, and triphenyltin hydroxide.

Usable moluscicides include, but are not limited to, metaldehyde, methiocarb and aluminium sulfate.

Usable miticides include, but are not limited to, antibiotic miticides, carbamate miticides, formamidine miticides, mite growth regulators, organochlorine, permethrin and organophosphate miticides.

Usable rodenticides include, but are not limited to, 2-isovalerylindan-1,3-dione, 4-(quinoxalin-2-ylamino)benzenesulfonamide, alpha-chlorohydrin, aluminium phosphines, anta, arsenics oxide, barium carbonate, bisthiosemi, brodifacoum, bromadiolone, bromethalin, calcium cyanide, chloralose, chlorophacinone, cholecalciferol, coumachlor, coumafuryl, coumatetralyl, crimidine, difenacoum, difethialone, diphacinone, ergocalciferol, flocoumafen, fluoroacetamide, flupropadine, flupropadine hydrochloride, gamma-HCH, HCH, hydrogen cyanide, iodomethane, lindane, magnesium phosphide, methyl bromide, norbormide, phosacetim, phosphine, phosphorus, pindone, potassium arsenite, pyrinuron, scilliroside, sodium arsenite, sodium cyanide, sodium fluoroacetate, strychnine, thallium sulfate, warfarin, and zinc phosphide.

Usable insect repellants include, but are not limited to, 2-ethyl-1,3-hexanediol; N-octyl bicycloheptene dicarboximide; N,N-diethyl-M-toluamide; 2,3:4,5-Bis(2-butylene) tetrahydro-2-furaldehyde; Di-n-propyl isocinchomeronate; and 2-hydroxyethyl-n-octyl sulfide. One skilled in the art, with the benefit of this disclosure will recognize suitable active ingredients for use with embodiments of the present invention.

In embodiments of the present invention, the agrochemical composition may be in a concentrated form that may be miscible or emulsifiable with water, such as an emulsifiable concentrate (EC) or a suspension concentrate (SC), for subsequent mixture with water at the application site. ECs are pesticide formulations containing an active ingredient and an emulsifying agent in an organic solvent. The solvent is usually not soluble in water. When an EC product is mixed with water prior to application, the resulting mix is a dispersion of fine, oily particles in water. SCs are stable suspensions of solid particulate active ingredients in water or an organic liquid. SCs are intended for dilution with water before use.

In embodiments of the present invention, other surfactants, stabilizers, promoters, fertilizers, and other desired compounds, which may be liquid or solid, may be added to the sticker adjuvants, spreader-sticker adjuvants and agrochemical compositions described herein. One skilled in the art will recognize other suitable compounds to add to the sticker adjuvants, spreader-sticker adjuvants and agrochemical compositions described herein.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the claims appended and any and all equivalents thereof. Therefore, any of the features and/or elements which are listed above may be combined with one another in any combination and still be within the breadth of this disclosure. The present invention will be further illustrated by a consideration of the following examples, which are intended to be exemplary of the invention.

EXAMPLES

Examples 1 to 6 are example sticker adjuvants of the present invention.

Example 1

61.045 grams (g) of UNIDYME™ 18 dimer acid and 97.5 g of JEFFAMINE® ED-900 polyetheramine were mixed together at room temperature and then heated to 240° C. for 5 hours under a slow stream of nitrogen gas. A volume of 3.0 mL of water was distilled over during the reaction and captured in a Dean-Stark trap. After 5 hours, the heat was removed and the reaction was cooled to 100° C. before stirring in 68.0 g of Aromatic 150 Fluid to facilitate pouring and handling. The resulting orange, viscous product mixture was 70% polymer and 30% Aromatic 150 Fluid. The polymer had a weight-average molecular weight ($M_w$) of 14,647, as determined by gel permeation chromatography (GPC).

Example 2

UNIDYME™ 18 dimer acid and JEFFAMINE® ED-600 polyetheramine were reacted using the method described in Example 1. The reaction product was again diluted with Aromatic 150 Fluid to 70%. The polymer had a $M_w$ of 15,695, as determined by GPC.

Example 3

UNIDYME™ 18 dimer acid and JEFFAMINE® ED-2003 polyetheramine were reacted using the method described in Example 1. The reaction product was again diluted with Aromatic 150 Fluid to 70%. The polymer had a $M_w$ of 10,564, as determined by GPC.

Example 4

UNIDYME™ 18 dimer acid and ELASTAMINE® HE-1000 amine were reacted using the method described in Example 1. The reaction product was again diluted with Aromatic 150 Fluid to 70%. The polymer had a $M_w$ of 3,146, as determined by GPC.

Example 5

UNIDYME™ 18 dimer acid and ELASTAMINE® HE-1700 amine were reacted using the method described in Example 1. The reaction product was again diluted with Aromatic 150 Fluid to 70%. The polymer had a $M_w$ of 3,754, as determined by GPC.

Example 6

79.8 g of Poly(isobutenyl)succinic anhydride (PIBSA), (80% diluted in naphthenic oil), was mixed with 44.7 g of ELASTAMINE® HE-1000 amine and heated to 220° C. for 5 hours under a slow stream of nitrogen gas. The naphthenic diluent oil as well as any water formed during the reaction was stripped off during this heating period. After 5 hours, the reaction was cooled to 150° C. and the viscous product was poured off into a storage vessel. This product was not diluted with solvent. The polymer had a $M_w$ of 5,257, as determined by GPC.

The following Comparative Examples are either current, commercial sticker adjuvant formulations known to be of use in the industry or current water-insoluble compounds that one skilled in the art would use as a sticker adjuvant.

Comparative Example 1

Alkoxylated alkylphenol condensate resin (POAR) formulated with a blend of Aromatic 150 Fluid, calcium dodecylbenzenesulfonate and linear alcohol ethoxylates.

Comparative Example 2

Linseed oil (Sigma Aldrich Corporation) was formulated with a blend of calcium dodecylbenzenesulfonate and linear alcohol ethoxylates to make an emulsifiable concentrate.

Comparative Example 3

A polyhydroxystearic acid derivative (PHSA) was formulated with a blend of Aromatic 150 Fluid, calcium dodecylbenzenesulfonate and linear alcohol ethoxylates.

Comparative Example 4

A sucrose polyester (SPE) was formulated with a blend of Aromatic 150 Fluid, calcium dodecylbenzenesulfonate, and linear alcohol ethoxylates.

The sticker adjuvants of Examples 1-6 were evaluated with regard to their adherence to leaf-like substrates. PARAFILM® M sealing film (available from Bemis Company, Inc. in Neenah, Wis.) was used to emulate a leaf surface. The sticker adjuvants of Examples 1-6 were formulated at 25% with a mixture of Aromatic 150 Fluid, MSO, calcium dodecylbenzenesulfonate, dioctylsulfosuccinate, and linear alcohol ethoxylates to create spreader-sticker emulsifiable concentrates (EC's). The different EC's were emulsified at 5% in water, and 200 μL of each emulsion was coated onto the PARAFILM® M sealing film and allowed to dry, after which it was dipped in water 100 times or 200 times at a rate of 1-2 dips per second. Then the film was allowed to dry. The mass of the substrate before coating, after coating, and after dipping was measured with an analytical balance and the retained mass of the coating was used to evaluate the performance of the spreader-sticker adjuvants that were formulated into ECs.

Table 1 below shows the data for the six Example spreader-sticker adjuvants mentioned above along with Comparative Examples 1 and 2. Table 1 shows that the six Examples show similar properties to Comparative Example 1 and improved properties over Comparative Example 2.

TABLE 1

| Sticker Adjuvant Type | % Mass Retained 100X dips | 200X dips |
|---|---|---|
| Examples | | |
| 1 (Dimer Acid + ED-2003) | 95.4 | 87.7 |
| 2 (Dimer Acid + ED-600) | 95.2 | 91.9 |
| 3 (Dimer Acid + ED-900) | 94.8 | 92 |
| 4 (Dimer Acid + HE-1000) | 91.8 | 90.5 |
| 5 (Dimer Acid + HE-1700) | 91.2 | 82.6 |
| 6 (PIBSA + HE-1000) | 91.7 | 87.5 |
| Comparative Examples | | |
| 1 (POAR) | 91.8 | 90 |
| 2 (Linseed oil) | 11.9 | 9.5 |

Figure 1A:
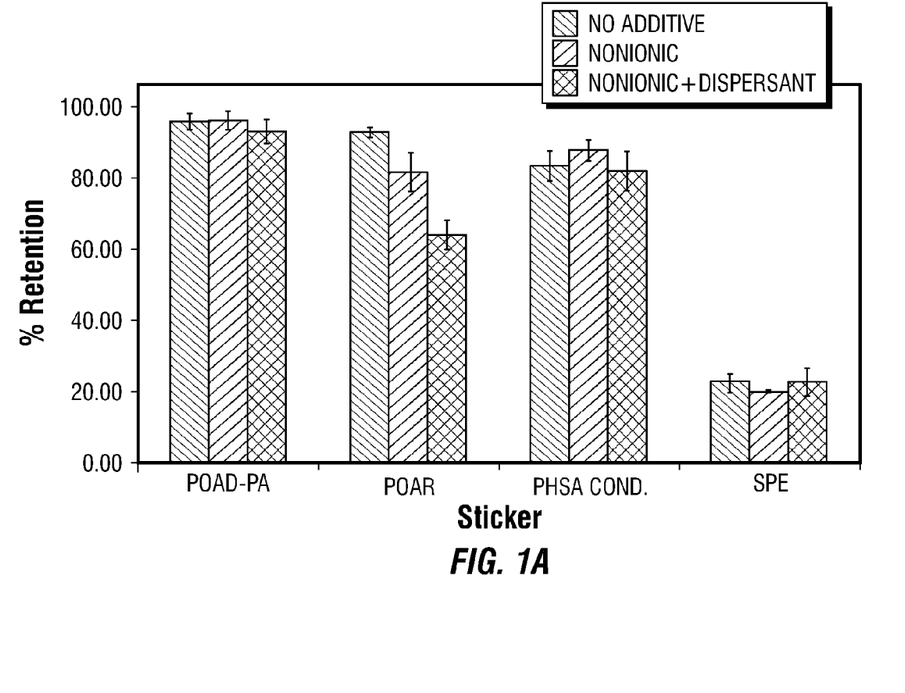
FIG. 1A is a graph showing percent mass retention versus sticker adjuvant type and formulation type for several sticker formulations after 100 dips in water.
Figure 1B:
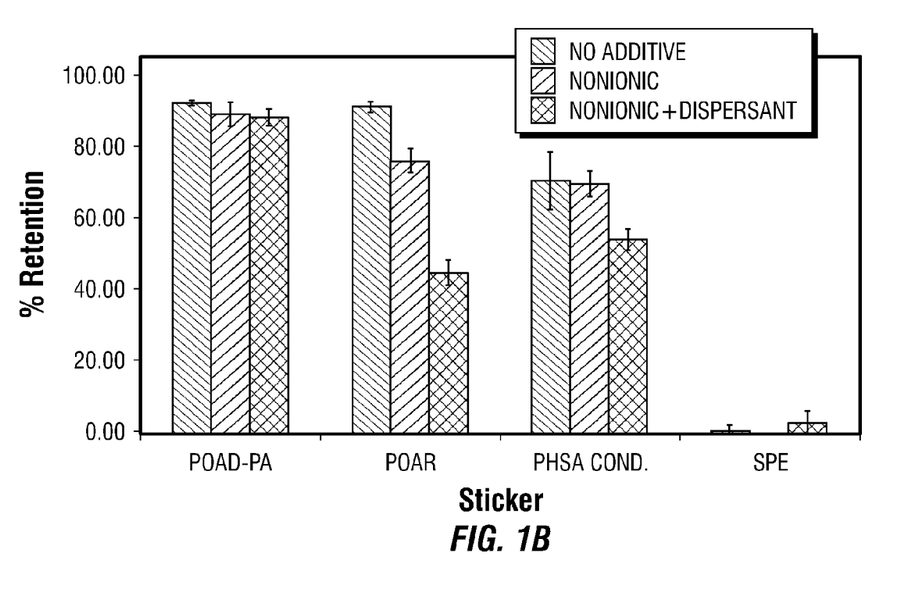
FIG. 1B is a graph showing percent mass retention versus sticker adjuvant type and formulation type for the sticker formulations of FIG. 1 after 200 dips in water.
Figure 2:
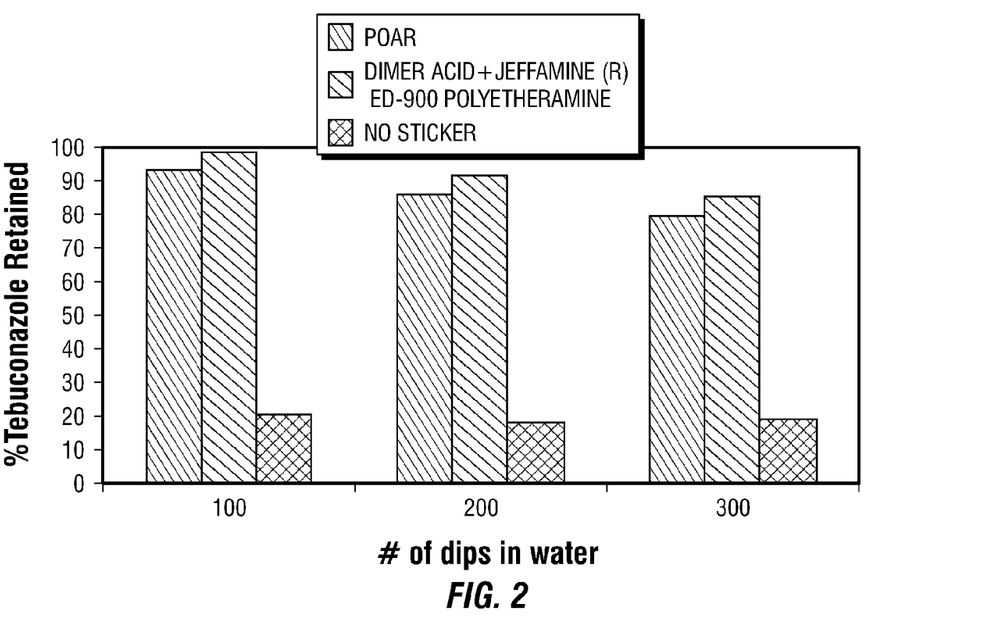
FIG. 2 is a graph showing percent mass retention of different tebuconazole fungicide formulations versus number of dips in water.
Figure 3:
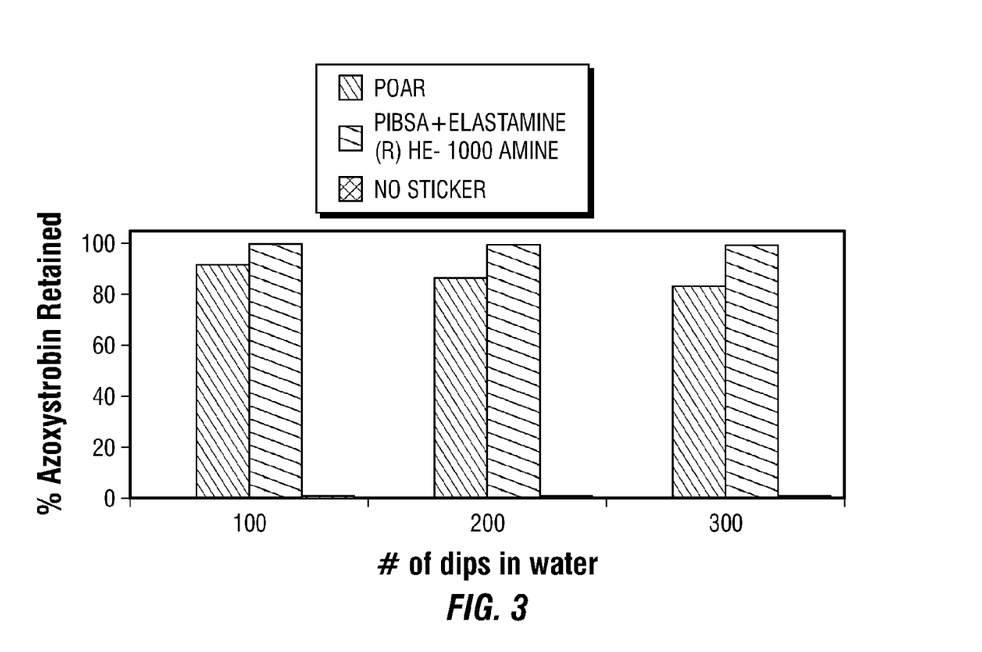
FIG. 3 is a graph showing percent mass retention of different Azoxystrobin fungicide formulations versus number of dips in water.

FIGS. 1A and 1B show mass retention versus sticker adjuvant type after dips in water. The same testing method using PARAFILM® M sealing film was used to produce the data of Table 1. Each sticker adjuvant was tested using no additive, in the presence of 0.65% SURFONIC® L24-12 surfactant (a high hydrophilic-lipophilic balance (HLB) nonionic surfactant additive), and additionally in the presence of 0.25% TERSPERSE® 2500 dispersant, a frequently used water-soluble dispersant. Results were generated to compare the sticker adjuvant described in Example 1, Comparative Example 1 (POAR), Comparative Example 3 (PHSA) and Comparative Example 4 (SPE).

FIG. 1A shows percent mass retention versus sticker adjuvant type after 100 dips in water. The data shows that the sticker adjuvant of Example 1 is retained at the highest percentage, especially in the presence of other water-soluble surfactants.

FIG. 1B shows percent mass retention versus sticker adjuvant type for the same sticker adjuvants in FIG. 1A after 200 dips in water. The sticker adjuvant of Example 1 performs favorably to the Comparative Examples 1, 3 and 4 after 200 dips in water. Example 1 may be a suitable replacement for Comparative Example 1 (POAR).

FIG. 2 shows percent mass retention of tebuconazole fungicide versus number of dips in water (100, 200 and 300) for Comparative Example 1, Example 3, and a Control (no sticker adjuvant).

To form the three test samples of FIG. 2, 0.5 g of a tebuconazole suspension concentrate (SC) was diluted into 20 g of deionized water, and 1.0 g of the appropriate sticker formulation was added to this sample and the mixture was inverted to mix the components. A 200 μL aliquot of this fungicide solution was then coated onto a piece of PARAFILM® M sealing film and allowed to dry overnight. The samples were then dipped 100×, 200×, or 300× into a beaker of deionized water as described above and allowed to dry again. The residue remaining on the substrate was dissolved in methanol and gas chromatography (GC) was used to determine how much tebuconazole was retained on the substrates.

FIG. 2 shows favorable performance of Example 3 with tebuconazole fungicide relative to the Comparative Example 1 (POAR) and the Control sample (no sticker adjuvant).

FIG. 3 shows percent mass retention of azoxystrobin fungicide versus number of dips in water (100, 200 and 300) for Comparative Example 1, Example 6, and a Control (no sticker adjuvant).

To form the three test samples of FIG. 3, 0.66 g of an azoxystrobin suspension concentrate (SC) was diluted into 20 g of deionized water, and 1.0 g of the appropriate sticker formulation was added to this sample and the mixture was inverted to mix the components. A 200 μL aliquot of this fungicide solution was then coated onto a piece of PARAFILM® M sealing film and allowed to dry overnight. The samples were then dipped 100×, 200×, or 300× into a beaker of deionized water as described above and allowed to dry again. The mass of the substrate before coating, after coating, and after dipping was measured with an analytical balance and the retained mass of the coating was used to evaluate the performance of the sticker adjuvants.

FIG. 3 shows favorable performance of Example 6 with azoxystrobin fungicide relative to Comparative Example 1 (POAR) and the Control sample (no sticker adjuvant). The Control samples shows that after 100 dips, there was no measurable azoxystrobin fungicide left on the film.

FIGS. 2 and 3, together, demonstrate favorable performance of the Example sticker adjuvants described herein compared to current commercial sticker adjuvants.

Although the present invention and its advantages have been described in detail, it should be understood that various changes, substitutions and alterations may be made herein without departing from the spirit and scope of the invention as defined by the appended claims.

The invention claimed is:

1. A sticker adjuvant comprising a polyether amide or a polyether imide formed by the reaction of a polyether polyamine with an acid anhydride comprising polyisobutenyl succinic anhydride, wherein the polyoxyalkylene diamine comprises the formula:

wherein x=2 to 8.

2. A sticker adjuvant comprising a polyether amide or a polyether imide formed by the reaction of a polyether polyamine with an acid anhydride comprising polyisobutenyl succinic anhydride, wherein the polyoxyalkylene diamine comprises the formula:

wherein y=5 to 40 and x+z=3 to 8.

3. A sticker adjuvant comprising a polyether amide or a polyether imide formed by the reaction of a polyether polyamine with an acid anhydride comprising polyisobutenyl succinic anhydride, wherein the polyoxyalkylene diamine comprises the formula wherein n=15 to 50.

4. The sticker adjuvant of claim 3 wherein the polyether polyamine has an average molecular weight of approximately 1000.

5. The sticker adjuvant of claim 1 wherein the polyether amide or the polyether imide is formed by the reaction of a polyether polyamine with the acid anhydride comprising polyisobutenyl succinic anhydride and a polyacid comprising a $C_6$-$C_{54}$ polycarboxylic acid or a dimerized fatty acid.

6. The sticker adjuvant of claim 5 wherein the polyacid is a dimerized fatty acid.

7. The sticker adjuvant of claim 1 wherein the polyether amide or polyether imide has a molecular weight of at least 1000.

8. A sticker adjuvant comprising a solvent and a polyether amide or a polyether imide formed by the reaction of a polyether polyamine with a polyfunctional monomer selected from the group consisting of: a polyacid, a difunctional acyl halide, an acid anhydride, a poly(acid anhydride) and a mixture thereof and wherein the solvent comprises a petroleum-based solvent, a methylated seed oil or a combination thereof.

9. The sticker adjuvant of claim 8 wherein the polyether polyamine comprises a polyoxyalkylene diamine.

10. The sticker adjuvant of claim 9 wherein the polyoxyalkylene diamine comprises the formula:

wherein x=2 to 8.

11. The sticker adjuvant of claim 9 wherein the polyoxyalkylene diamine comprises the formula:

wherein y=5 to 40 and x+z=3 to 8.

12. The sticker adjuvant of claim 8 wherein the polyether polyamine comprises the formula:

wherein n=15 to 50.

13. The sticker adjuvant of claim 12 wherein the polyether polyamine has an average molecular weight of approximately 1000.

14. The sticker adjuvant of claim 8 wherein the polyacid comprises a $C_6$-$C_{54}$ polycarboxylic acid.

15. The sticker adjuvant of claim 8 wherein the polyacid comprises a dimerized fatty acid.

16. The sticker adjuvant of claim 8 wherein the acid anhydride comprises a $C_6$-$C_{54}$ acid anhydride.

17. The sticker adjuvant of claim 8 wherein the acid anhydride comprises polyisobutenyl succinic anhydride.

18. The sticker adjuvant of claim 8 wherein the polyether amide or polyether imide has a molecular weight of at least 1000.

19. The sticker adjuvant of claim 2 wherein the polyether amide or the polyether imide is formed by the reaction of a polyether polyamine with the acid anhydride comprising polyisobutenyl succinic anhydride and a polyacid comprising a $C_6$-$C_{54}$ polycarboxylic acid or a dimerized fatty acid.

20. The sticker adjuvant of claim 19 wherein the polyacid is a dimerized fatty acid.

21. The sticker adjuvant of claim 3 wherein the polyether amide or the polyether imide is formed by the reaction of a polyether polyamine with the acid anhydride comprising polyisobutenyl succinic anhydride and a polyacid comprising a $C_6$-$C_{54}$ polycarboxylic acid or a dimerized fatty acid.

22. The sticker adjuvant of claim 21 wherein the polyacid is a dimerized fatty acid.

* * * * *